(12) United States Patent
Devincenzo

(10) Patent No.: US 7,001,179 B2
(45) Date of Patent: Feb. 21, 2006

(54) ORTHODONTIC BRACKET AND CLIP

(76) Inventor: John Devincenzo, 1312 Garden St., San Luis, Obispo, CA (US) 93401

( * ) Notice: Subject to any disclaimer, the term of this patent is extended or adjusted under 35 U.S.C. 154(b) by 252 days.

(21) Appl. No.: 10/373,819

(22) Filed: Feb. 25, 2003

(65) Prior Publication Data

US 2004/0166457 A1  Aug. 26, 2004

(51) Int. Cl.
*A61C 3/00* (2006.01)

(52) U.S. Cl. .......................... 433/11; 24/563

(58) Field of Classification Search ................ 433/11, 433/8–10, 12–16; 24/563, 570, 67.3, 67.9, 24/456, 458, DIG. 8, DIG. 9, 571
See application file for complete search history.

(56) References Cited

U.S. PATENT DOCUMENTS

| 1,331,654 | A | * | 2/1920 | League ......................... 2/302 |
| 3,871,096 | A | * | 3/1975 | Wallshein ..................... 433/11 |
| 3,959,880 | A | * | 6/1976 | Andrews ....................... 433/11 |
| 4,023,274 | A | * | 5/1977 | Wallshein ..................... 433/11 |
| 4,144,642 | A | * | 3/1979 | Wallshein ..................... 433/11 |
| 4,710,852 | A | * | 12/1987 | Keen ........................... 381/717 |
| 5,967,773 | A | | 10/1999 | Roman et al. |
| 6,190,166 | B1 | * | 2/2001 | Sasakura ....................... 433/14 |

* cited by examiner

*Primary Examiner*—John J Wilson
(74) *Attorney, Agent, or Firm*—Rodgers & Rodgers

(57) ABSTRACT

An orthodontic bracket comprising a pair of tie wings, an archwire containing slot disposed between the tie wings, a pair of gingival stabilizing notches formed in one of the tie wings, an incisal stabilizing slot formed in the other tie wing, an orthodontic clip comprising an interactive section with a gingival wing secured to one side edge thereof and an incisal wing secured to the other side thereof, a medial slit formed in interactive section, a pair of supplemental slits formed between the interactive section and the gingival wing and the incisal wing, respectively, portions of the gingival wing disposed in the gingival stabilizing notches, and a portion of the incisal wing disposed in the incisal stabilizing slot.

13 Claims, 3 Drawing Sheets

ORTHODONTIC BRACKET AND CLIP

BACKGROUND OF THE INVENTION

In the field of orthodontics, the archwire is attached to an orthodontic bracket which in turn is cemented or otherwise attached to a patient's tooth. A precise slot is formed in the center portion of the bracket through which the archwire passes. The archwire is cylindrical or quadrilateral in shape to fit into the corresponding slot in the bracket. Historically, the archwire has been fastened to the bracket by means of ligature wires. Over time and after multiple tightening or replacement procedures, the tooth gradually moves towards the archwire until complete engagement has been obtained. By this means, eventually the bracket slot is fully engaged to the archwire.

More recently, flexible archwires have been utilized which provide more rapid engagement of the archwire into the bracket slot, thereby moving individual teeth more quickly. These elastic archwires often contain nickel and titanium alloys. Another means of attaching the archwire to the bracket is by means of plastic rings called Alastics or O-rings. These rings loop around the tie wings of the bracket and thereby draw the archwire tightly to the bracket.

Also, recently a new family of orthodontic brackets was introduced which are self-ligating thereby eliminating the need for ligatures or Alastics. By this means, a movable sleeve, contained within the bracket, forces locks the archwire into the bracket slot resulting in a more rapid placement, removal and adjustment of the archwires, thereby by saving the clinician valuable time. Another advantage of the self-ligating brackets is greatly reduced friction thereby allowing the tooth to slide more easily during certain movements. This can be accomplished with reduced force and results in shorter treatment times.

Although reduced friction from the self-ligating brackets is often desirable, sometimes more friction is desired such as near the end of treatment when small adjustments in the teeth are necessary and when other teeth are utilized as stabilizing anchor units. With frictionless brackets, the desired stability is not available and, therefore, toward the end of the treatment cycle tooth movement time is extended. Another disadvantage of the self-ligating brackets is that they include moving parts which become distorted, warped or disengaged. This in turn requires clinical modifications or placement of more conventional brackets as treatment proceeds.

BRIEF SUMMARY OF THE INVENTION

By this invention, a bracket is provided and includes a base with a support integrally joined thereto and extending therefrom, spaced tie wings secured to the support with an archwire containing slot formed therebetween, superior stabilizing notches formed in the incisal tie wings, and gingival stabilizing slots formed in the other tie wings.

Also, in accordance with this invention, an orthodontic clip is provided having an interactive section with a medial slot formed therein, a gingival wing and an incisal wing integrally joined, respectively, to opposite sides of the interactive section, and supplemental slits formed between the interactive section and the wings, respectively.

BRIEF DESCRIPTIONS OF THE SEVERAL VIEWS OF THE DRAWINGS

DETAILED DESCRIPTION OF THE INVENTION

Figure 8:
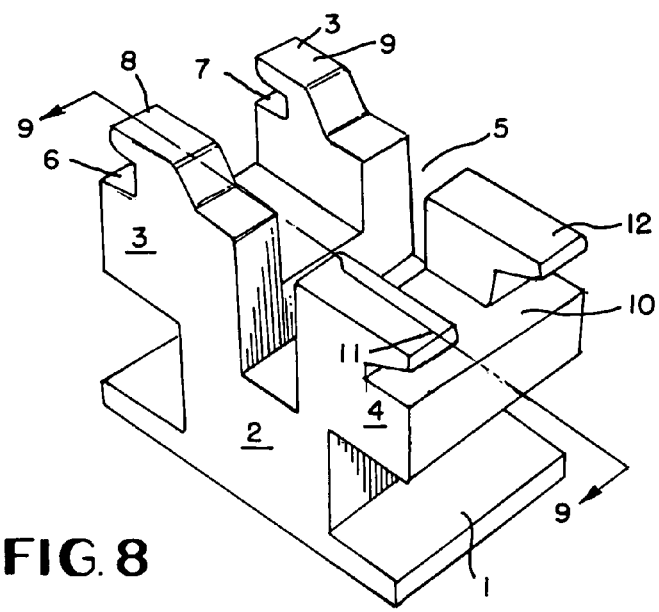
FIG. 8 is a perspective view of the bracket according to this invention.
Figure 9:
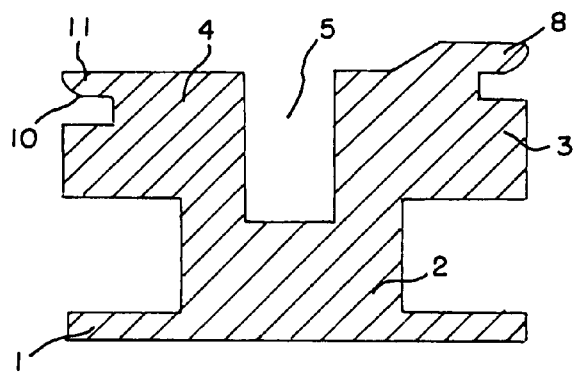
FIG. 9 is a view taken along line 9—9 in FIG. 8.
Figure 10:
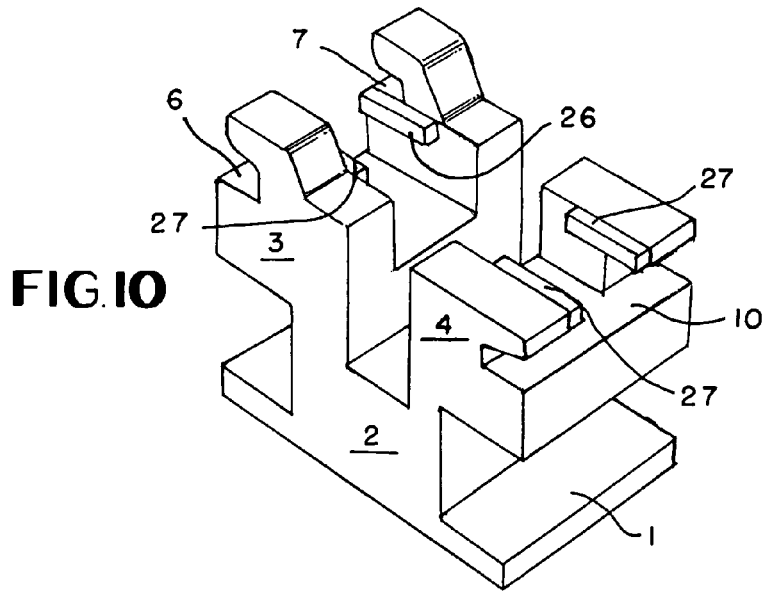
FIG. 10 is a perspective view showing a modification of the bracket.

In the drawings and with particular reference to FIGS. 8, 9 and 10 wherein the bracket according to this invention is shown, the numeral 1 designates the bracket base with support 2 integrally joined thereto and extending outwardly therefrom. Spaced tie wings 3 and tie wing 4 are integrally joined to support 2 remote from base 1. Archwire containing slot 5 is formed in the bracket intermediate tie wings 3 and 4, as is well known. According to this invention, gingival stabilizing notches 6 and 7 are formed in tie wings 3, respectively, by means of retention tabs 8 and 9 which extend gingivally from tie wings 3 and outwardly therefrom.

To the complete basic elements of the bracket according to this invention, incisal stabilizing slot 10 is formed in tie wing 4. Also the gingival end edges of tabs 8 and 9 and the incisal spaced portions 11 and 12 of incisal stabilizing slot 10 are rounded, as best shown in FIGS. 8 and 9.

Figures 2, 3:
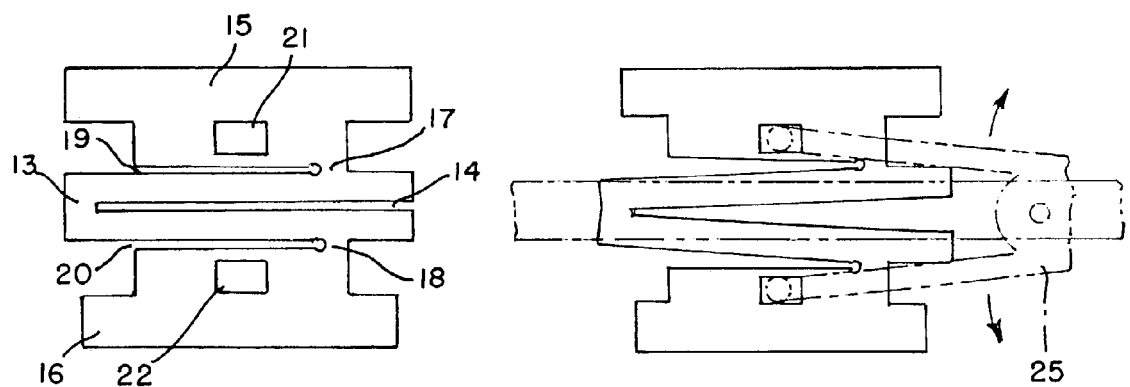
FIG. 2 is a plan view of the clip.
FIG. 3 is a plan view showing the clip being activated by installation and removal tool shown in dotted lines.

Another aspect of this invention is the orthodontic clip, as best shown in FIG. 2, which includes interactive center section 13 with medial slit 14 formed therein. Gingival wing 15 and incisal wing 16 are integrally joined to the side edges of interactive center section 13 at junctions 17 and 18, respectively. Supplemental slit 19 is formed between gingival wing 15 and interactive section 13 and, likewise, supplemental slit 20 is formed between incisal wing 16 and interactive center section 13.

Both slits 19 and 20 are shorter than medial slit 14 such that slits 19 and 20 result in the same summation of movement as medial slit 14. Therefore, when the clip is expanded, gingival wing 15 and incisal wing 16 move outwardly of the clip in a proportional and parallel fashion, as best shown in FIG. 3. To complete the basic elements of the clip, apertures 21 and 22 are formed, respectively, in gingival wing 15 and incisal wing 16.

Figure 4:
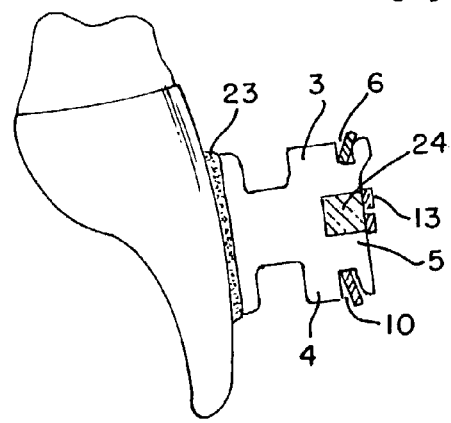
FIG. 4 is a cross-sectional view taken along line 4—4 in FIG.
Figure 5:
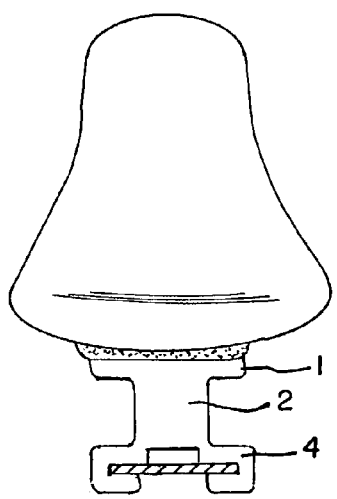
FIG. 5 is a cross-sectional view taken along line 5—5 in FIG. 1.
Figure 6:
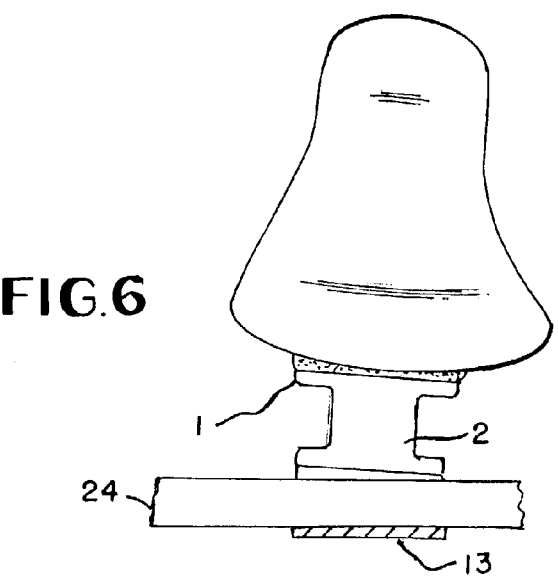
FIG. 6 is a cross-sectional view showing a rotated tooth not completely engaged in the bracket archwire slot.

In actual practice and as shown in FIG. 4, the bracket is first adhered to a patient's tooth by means of conventional adhesive 23, as is well known. Then archwire 24 is positioned in proximity to archwire containing slot 5. As a result, the elements appear as best shown in FIG. 6.

Figure 1:
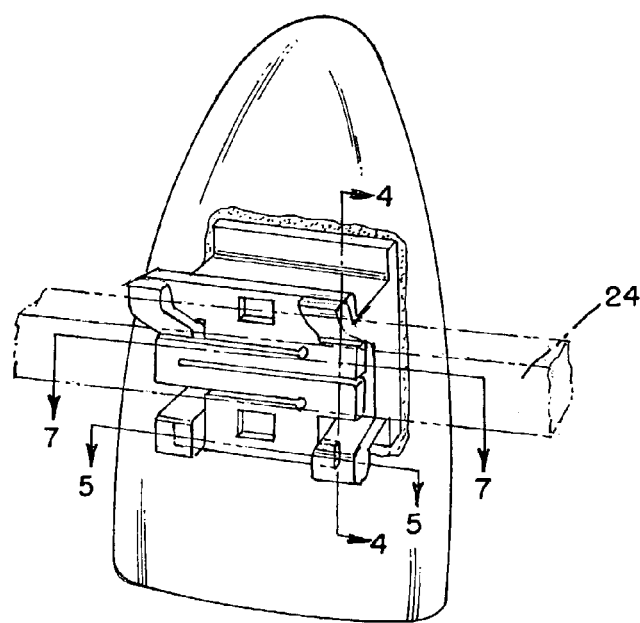
FIG. 1 is a perspective view of the orthodontic bracket and clip according to this invention.

Following this and in accordance with this invention, the orthodontic clip gingival wing 15 is inserted into gingival stabilizing notches 6 and 7, as best shown in FIG. 1. The ends of installation and removal tool 25 are then inserted into apertures 21 and 22 and the tool is manipulated to cause the expansion of the orthodontic clip wherein gingival wing 15 and incisal wing 16 are separated by means of the expansion of medial slit 14 and supplemental slits 19 and 20, as best shown in FIG. 3.

Then the clip is extended over archwire 24 and incisal wing 16 is inserted into incisal stabilizing slots 10. Due to the resiliency of the orthodontic clip, wings 15 and 16 are urged toward each other. Since gingival stabilizing notches 6 and 7 extend more labially than inferior stabilized slot 10, the orthodontic clip is bent or deformed as it extends around archwire 24.

This feature facilitates the manipulation of tool 25 and prevents the center portion of the clip from moving toward the bottom of archwire slot 5. A modification of the bracket is shown in FIG. 10, wherein ledges 26 and 27 are formed on the interior surfaces of tie wings 3 and 4, respectively.

Figure 7:
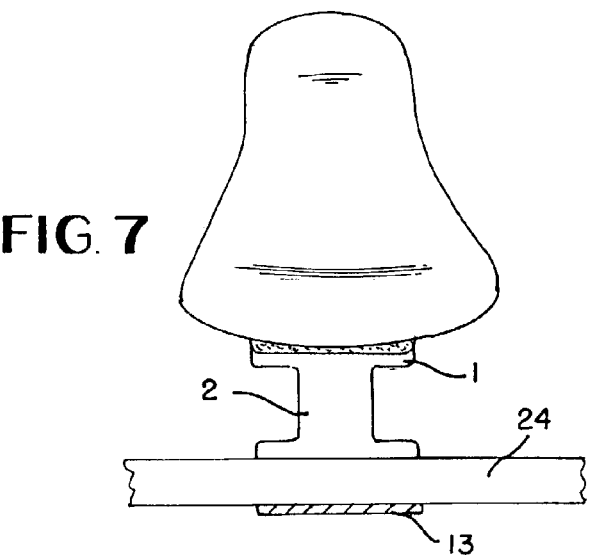
FIG. 7 is a cross-sectional view taken along the line 7—7 in FIG. 1.

Therefore, in accordance with this invention, the orthodontic clip exerts a force on archwire 24 which is transmitted through gingival wing 15 and incisal wing 16 onto interactive center section 13, then through the bracket and to the tooth thereby causing the tooth to be drawn toward archwire 24 which results in the rotational or linear movement of the tooth, as desired and as shown in the change in tooth rotation from FIG. 6 to FIG. 7. If archwire 24 is more flexible than the orthodontic clip, the archwire will temporarily deform until the tooth moves to a position wherein the archwire is no longer deformed.

This change in the archwire slot relationship can be seen in FIG. 6 wherein the archwire is initially inserted and in FIG. 7 wherein the force of the interactive clip has moved the tooth to fill the archwire slot.

What is claimed is :

1. An orthodontic appliance comprising a bracket including a pair of spaced tie wings, at least one gingival stabilizing notch formed in one of said tie wings, an incisal stabilizing slot formed in the other of said tie wings, a planar orthodontic clip including an interactive section with a gingival wing and an incisal wing integrally joined to the side edges of said interactive section respectively, a supplemental slit formed in said clip between one of said wings and said interactive section, and a portion of said gingival wing disposed in said gingival stabilizing notch and a portion of said incisal wing disposed in said incisal stabilizing slot.

2. An orthodontic appliance according to claim 1 wherein said incisal stabilizing slot comprises a pair of spaced portions.

3. An orthodontic appliance according to claim 2 wherein said retention tabs and said spaced portions are rounded.

4. An orthodontic appliance according to claim 1 wherein a pair of supplemental slits are formed in said clip and wherein said supplemental slits are disposed between said interactive section and said gingival wing and said incisal wing respectively.

5. An orthodontic appliance according to claim 4 wherein said supplemental slits are shorter than said medial slit.

6. An orthodontic appliance according to claim 1 wherein a medial slit is formed in said interactive section.

7. An orthodontic appliance according to claim 6 wherein a pair of supplemental slits are disposed on opposite sides of said medial slit.

8. An orthodontic appliance according to claim 1 wherein a pair of apertures are formed in said gingival wing and said incisal wing respectively.

9. An orthodontic appliance according to claim 1 wherein ledges are formed on the interior surfaces of said tie wings, respectively.

10. An orthodontic appliance according to claim 1 wherein said gingival stabilizing notch is formed by an upwardly and outwardly extending retention tab.

11. An orthodontic appliance comprising a bracket including a pair of spaced tie wings, at least one gingival stabilizing notch formed in one of said tie wings, an incisal stabilizing slot formed in the other of said tie wings, an orthodontic clip including an interactive section with a gingival wing and an incisal wing integrally joined to the side edges of said interactive section respectively, a portion of said gingival wing disposed in said gingival stabilizing notch, a portion of said incisal wing disposed in said incisal stabilizing slot, and a medial slit formed in said interactive section.

12. An orthodontic appliance according to claim 11 wherein a pair of supplemental slits are disposed on opposite sides of said medial slit.

13. An orthodontic appliance comprising a bracket including a pair of spaced tie wings, at least one gingival stabilizing notch formed in one of said tie wings, an incisal stabilizing slot formed in the other of said tie wings, an orthodontic clip including an interactive section with a gingival wing and an incisal wing integrally joined to the side edges of said interactive section respectively, a portion of said gingival wing disposed in said gingival stabilizing notch, a portion of said incisal wing disposed in said incisal stabilizing slot, and a pair of apertures formed in said gingival wing and said incisal wing respectively.

* * * * *